(12) United States Patent
Thompson

(10) Patent No.: US 11,660,000 B2
(45) Date of Patent: May 30, 2023

(54) METHOD FOR DETECTING FLUID INJECTION IN A PATIENT

(71) Applicants: TTAAS THOMMO'S TRAINING & ASSESSMENT SYSTEMS PTY LTD, Mount Victoria (AU); T&T GLOBAL SOLUTIONS PTY LTD, Mount Victoria (AU)

(72) Inventor: Wayne Thompson, Warners Bay (AU)

(73) Assignee: Quaker Chemical (Australasia) Pty Ltd, Seven Hills (AU)

( * ) Notice: Subject to any disclaimer, the term of this patent is extended or adjusted under 35 U.S.C. 154(b) by 214 days.

(21) Appl. No.: 16/989,661

(22) Filed: Aug. 10, 2020

(65) Prior Publication Data

US 2020/0367755 A1  Nov. 26, 2020

Related U.S. Application Data

(60) Division of application No. 15/798,917, filed on Oct. 31, 2017, now abandoned, which is a continuation of
(Continued)

(30) Foreign Application Priority Data

Sep. 2, 2011 (AU) ................. 2011-903536

(51) Int. Cl.
*A61B 5/00* (2006.01)
*G01M 3/20* (2006.01)
(Continued)

(52) U.S. Cl.
CPC .......... *A61B 5/0071* (2013.01); *A61B 5/4845* (2013.01); *A61M 5/007* (2013.01);
(Continued)

(58) Field of Classification Search
CPC ....... A61B 5/0071; A61B 5/06; A61B 5/4845; A61M 5/007; F02M 2200/18; F15B 20/005; F15B 21/06; G01M 3/20; G01N 21/643
See application file for complete search history.

(56) References Cited

U.S. PATENT DOCUMENTS 5,421,192 A  6/1995 Henry
6,056,162 A  5/2000 Leighley
(Continued)

FOREIGN PATENT DOCUMENTS

CA  879597 A  8/1971
CN  102099671 A  6/2011
(Continued)

OTHER PUBLICATIONS

Office Action for corresponding Canadian Patent Application No. 2,883,777 dated Mar. 8, 2018, 4 pages.
(Continued)

*Primary Examiner* — Mark D Remaly
(74) *Attorney, Agent, or Firm* — Morgan, Lewis & Bockius LLP

(57) ABSTRACT

A method for detecting fluid injection in a patient, the method including the steps of providing a fluid storage tank; providing fluid for use in machinery and adding said fluid to the fluid storage tank; and providing a fluorescent dye and adding the fluorescent dye to the fluid such that the fluid fluoresces in the presence of ultraviolet light.

10 Claims, 6 Drawing Sheets

Related U.S. Application Data application No. 15/051,932, filed on Feb. 24, 2016, now abandoned, which is a continuation of application No. 14/238,171, filed as application No. PCT/AU2012/000094 on Feb. 2, 2012, now abandoned.

(51) Int. Cl.

| | |
|---|---|
| *F15B 20/00* | (2006.01) |
| *A61M 5/00* | (2006.01) |
| *G01N 21/64* | (2006.01) |
| *F15B 21/06* | (2006.01) |

(52) U.S. Cl.
CPC ............ *F15B 20/005* (2013.01); *G01M 3/20* (2013.01); *F02M 2200/18* (2013.01); *F15B 21/06* (2013.01); *G01N 21/643* (2013.01); *G01N 2021/6439* (2013.01)

(56) References Cited

U.S. PATENT DOCUMENTS

| | | | |
|---|---|---|---|
| 6,165,384 | A | 12/2000 | Cooper et al. |
| 9,011,716 | B1 | 4/2015 | Duerr |
| 2003/0044523 | A1 | 3/2003 | Brass |
| 2005/0094147 | A1 | 5/2005 | Yaroslavsky et al. |
| 2010/0071891 | A1 | 3/2010 | Liknes |
| 2011/0117025 | A1 | 5/2011 | Dacosta et al. |
| 2013/0062563 | A1 | 3/2013 | Zhou et al. |

FOREIGN PATENT DOCUMENTS

| | | |
|---|---|---|
| EP | 2098156 A1 | 9/2009 |
| JP | H08128916 A | 5/1996 |
| JP | H1130594 A | 2/1999 |
| RU | 2007104289 A | 8/2008 |
| RU | 2014105444 A | 10/2015 |
| WO | 9207249 A1 | 4/1992 |
| WO | 2005027730 A2 | 3/2005 |
| WO | 2005052560 A1 | 6/2005 |
| WO | 2013029082 A1 | 3/2013 |

OTHER PUBLICATIONS

English Translation of Office Action for corresponding Russian Patent Application No. 2017145799 dated Mar. 29, 2021, 7 pages.
English Translation of Search Report for corresponding Russian Patent Application No. 2017145799 dated Mar. 25, 2021, 2 pages.
European Search Report for EP 20155942; dated Jul. 15, 2020; 2 pages.
European Search Opinion for EP 20155942; dated Jul. 15, 2020; 8 pages.
Aragon et al., "Reliability of a Visual Scoring System with Fluorescent Tracers to Assess Dermal Pesticide Exposure", Ann. Occup. Hyg., vol. 48, No. 7, pp. 601-606 (2004).
Aragon et al., "Assessment of Dermal Pesticide Exposure with Fluorescent Tracer: A Modification of a Visual Scoring System for Developing Countries", Ann. Occup. Hyg., vol. 50, No. 1, pp. 75-83 (2006).
Cherrie et al., "Use of Qualitative and Quantitative Fluorescence Techniques to Assess Dermal Exposure", Ann. Occup. Hyg., vol. 44, No. 7, pp. 519-522 (2000).
Crismon et al., "Studies of Gangrene Following Cold Injury. V. The Use of Fluorescein as an Indicator of Local Blood Flow: Fluorescein Tests in Experimental Frostbite", Sep. 1, 1946, pp. 268-276.
Davis, Pinpointing Vehicle Leaks Faster with Ultraviolet Light, Materials Evaluation, vol. 47, pp. 1248-1250 (1989).
Doyle, "A System for the Management of Ricks from Pressurised Fluids", NSW Minerals Council—Occupational Health & Safety Conference, Jul. 2011.
Fenske, "Visual Scoring System for Fluorescent Tracer Evaluation of Dermal Exposure to Pesticides", Bull. Environ Contam. Toxicol., vol. 41, pp. 727-736 (1988).
Fenske, "Dermal Exposure Assessment Techniques", Ann. Occup. Hyg., vol. 37, No. 6, pp. 687-706 (1993).
Fenske, "Nonuniform Dermal Deposition Patterns during Occupational Exposure to Pesticides", Arch. Environ. Contam. Toxicol., vol. 19, pp. 332-337 (1990).
Jonak et al., "Intradermal Indocyanine Green for In Vivo Fluorescence Laser Scanning Microscopy of Human Skin: A Pilot Study", PLoS ONE, vol. 6, No. 8, e23972 (2011).
Karlbauer et al., "High-Pressure Injection Injury: A Hand-Threatening Emergency", The Journal of Emergency Medicine, vol. 5, pp. 375-379 (1987).
Marrano, "Fluorescent Tracer Additives as a Nondestructive Inspection Technique for Leak Testing", Materials Evaluation, pp. 436-438 (1993).
Semple, "Dermal Exposure to Chemicals in the Workplace: Just How Important is Skin Absorption?", Occup Environ Med, vol. 61, pp. 376-382 (2004).
Spectroline Corporation, "Fluorescent Leak Detection for Industrial Systems", May 20, 2010 http://web.archive.org/web/20100529021051/http://www.spectroline.com/industrial/industrialproducts.html.
Swindle et al., "View of Normal Human Skin In Vivo as Observed Using Fluorescent Fiber-Optic Confocal Microscopic Imaging", The Journal of Investigative Dermatology, vol. 121, No. 4, pp. 706-712 (2003).
Vo-Dinh et al., "The lightpipe luminoscope for monitoring occupational skin contamination", Am. Ind. Hyg. Assoc. J., vol. 42, pp. 112-120 (1981).
International Search Report for PCT/AU2012/000094 dated Mar. 26, 2012.
European Search Report for Application EP 12 82 7019 dated Mar. 20, 2015.
Magnusson et al., "Broad and complex antifungal activity among environmental isolates of lactic acid bacteria", FEMS Microbiology Letters, vol. 219, pp. 129-135 (2003).
Schnuerer et al., "Antifungal lactic acid bacteria as biopreservatives", Trends in Food Science & Technology, vol. 16, pp. 70-78 (2005) Abstract Only.
Vasilevski et al., "High-Pressure Injection Injuries to the Hand", Am J Emerg Med, vol. 18, pp. 820-824 (2000).
Verhoeven et al., "High-Pressure Injection Injury of the Hand: An Often Underestimated Trauma: Case Report with Study of Literature", Strat Traum Limb Recon, vol. 3, pp. 27-33 (2008).
English-language abstract of JPH08128916 (1996).
English-language abstract and translation of JPH11030594 (1999).
Office Action for Russian Application No. 2017145799 dated Aug. 2, 2021, 8 pages.
Jonak, C. et al., "Intradermal Indocyanine Green for In Vivo Fluorescence Laser Scanning Microscopy of Human Skin: A Pilot Study," PLoS One, 2011, 6(8):e23972.
Technical Opinion for Brazilian Application No. 112014004260-8 dated Aug. 4, 2021, 4 pages.
Dan et al., "1% Lymphazurin vs 10% Fluorescein for Sentinel Node Mapping in Colorectal Tumors," Arch. Surg., 2004, 130:1180-1184.
Rohm and Haas, "Flourescent Yellow 131SC Product Descriptor," Oct. 2006, pp. 3.
Commonwealth of Australia, "Statutory Declaration made by Glen Lilly," dated May 20, 2014.
Office action issued in pending Canadian application No. 2,883,777 dated Mar. 8, 2018.
Office Action for Russian Application No. 2017145799 dated Nov. 26, 2021, 14 pages.
Denial for Brazilian Application No. 112014004260-8 dated Nov. 25, 2021, 5 pages.

METHOD FOR DETECTING FLUID INJECTION IN A PATIENT

CROSS-REFERENCE TO RELATED APPLICATIONS

The present invention is a divisional of U.S. patent application Ser. No. 15/798,917 filed on Oct. 31, 2017, which is a continuation of U.S. patent application Ser. No. 15/051,932 filed on Feb. 24, 2016, which is a continuation of U.S. patent application Ser. No. 14/238,171, filed on Feb. 10, 2014, which is a national stage application of PCT/AU2012/000094, filed Feb. 2, 2012, which claims priority to Australian Patent Application No. 2011903536, filed Sep. 2, 2011, all of the disclosures of which are hereby incorporated by reference in their entireties.

FIELD OF THE INVENTION

The present invention relates to the detection of fluid in the human body and in particular to the detection of hydraulic and fuel fluid within the human body. The invention has been developed primarily for use in detecting the presence of hydraulic and diesel fuel in the human body as a result accidental fluid injection and will be described hereinafter with reference to this application. However, it will be appreciated that the invention is not limited to this particular field of use.

BACKGROUND OF THE INVENTION in this specification unless the contrary is expressly stated, where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Hydraulic and diesel fuel systems machinery such as those in mining and other industrial areas, operate at very high pressures, often 207 bar (3000 psi) and above. Loose connections or defective hoses can cause a fine, high velocity stream of fluid. Testing has shown that even in systems pressurised to as little as 7 bar (100 psi), this fluid stream can penetrate human skin.

The injury sustained in a high pressure injection incident is usually worse than it will first appear. The injury is relatively rare and it may be that some medical practitioners or hospital services will not be alert to the severity of an injury of this type.

An accidental fluid injection beneath the skin may initially only produce a slight stinging sensation. The danger is that a victim will tend to ignore this, thinking that it will get better with time. This is not often the case and the fluid can cause serious tissue damage. Fluid injected directly into a blood vessel can spread rapidly through a victim's circulatory system leaving the human body with little ability to purge these types of fluid.

A fluid injection injury can become very serious or even fatal if not dealt with promptly and properly. Typically the only treatment available is to surgically remove the fluid within a few hours of injection. The longer the delay in getting professional medical aid, the further the tissue damage can spread. If left untreated, the injury could result in disfigurement, amputation of the affected part or death of the victim.

Accidental fluid injections can be difficult to confirm. That is, victims may be covered by fluid externally however there may be uncertainty on whether any fluid has penetrated the victim's skin. As discussed above any delay in treating a victim can cause severe harm and as such it would be advantageous if confirmation of fluid injection can be confirmed.

SUMMARY OF THE INVENTION

It is an object of the present invention to overcome or ameliorate at least one of the disadvantages of the prior art, or to provide a useful alternative.

According to a first aspect of the invention there is provided a method for detecting fluid injection in a patient, the method including the steps of:
 providing a fluid storage tank;
 providing fluid for use in machinery and adding said fluid to the fluid storage tank; and
 providing a fluorescent dye and adding the fluorescent dye to the fluid such that the fluid fluoresces in the presence of ultraviolet light.

Preferably the method includes the step of providing a fluorescent light to detect the presence of the fluid.

Preferably the light is a high intensity blue light.

Preferably the method includes the step of a possible fluid injection occurring in a patient.

Preferably the method includes the step of providing a dark room and examining the patient with the blue light in the dark room to determine whether possible fluid injection has occurred.

Preferably the method includes the step of washing the patient.

Preferably the method includes the step of washing the point of possible fluid injection on the patient.

Preferably the method includes the step of examining the patient with the blue light in the dark room to determine whether possible fluid injection has occurred after the step of washing the patient.

Preferably the method includes the step of determining whether or not fluid injection has occurred.

According to a second aspect of the invention there is provided a fluid reservoir, the fluid reservoir adapted to store hydraulic fluid and fluorescent dye such that the hydraulic fluid and the fluorescent dye mix in the fluid reservoir.

Preferably the fluid reservoir is connected to and in fluid communication with at least one hydraulic actuator and/or motor such that the flow of hydraulic fluid and the fluorescent dye such drives the actuator and/or motor.

Preferably the fluid reservoir is connected to the at least one hydraulic actuator and/or motor by at least one of the following: a hydraulic tube; a hydraulic pipe; or a hydraulic hose.

Preferably a leak in the hydraulic tube, hydraulic pipe or hydraulic hose results in both hydraulic fluid and fluorescent dye leaking there from.

According to a third aspect of the invention there is provided hydraulic machinery including the fluid reservoir described above.

According to a third aspect of the invention there is provided a method for detecting leaks in a hydraulic system, the method including the steps of:
 providing a fluid storage tank;
 providing fluid for use in machinery and adding said fluid to the fluid storage tank; and providing a fluorescent dye and adding the fluorescent dye to the fluid such that the fluid fluoresces in the presence of ultraviolet light.

According to a fourth aspect of the invention there is provided a method for detecting leaks in a hydraulic system, the method including the steps of:
providing a fluid storage tank;
providing fluid for use in machinery and adding said fluid to the fluid storage tank; and
providing a colouring dye and adding the colouring dye to the fluid such that the fluid changes colour.

Preferably the fluid changes colour to a colour that can be easily detected if a leak occurs in the hydraulic system.

According to a fifth aspect of the invention there is provided a fluid reservoir, the fluid reservoir adapted to store hydraulic fluid and a dye having a colour characteristic such that the hydraulic fluid and the dye mix in the fluid reservoir thereby causing the fluid to change colour according to the colour characteristics of the dye.

According to a sixth aspect of the invention there is provided a method for detecting leaks in a hydraulic machine, the method including the steps of:
providing a fluid reservoir having a hydraulic fluid therein, the reservoir being in fluid communication with the hydraulic machine;
adding a dye having colour characteristics to the fluid reservoir such that the hydraulic fluid takes on the colour characteristics of the dye.

According to a seventh aspect of the invention there is provided a method for detecting leaks in a fluid flow system; the method including the steps of:
providing a fluid reservoir having a fluid therein, the reservoir being in fluid communication with the system;
adding a dye having colour characteristics to the fluid reservoir such that the fluid takes on the colour characteristics of the dye thereby allowing a user to identify leaks in the system.

Preferably the liquid is chosen from one or more of the following liquids: water; hydraulic fluid; petrol; diesel; and any other suitable fluid.

According to an eighth aspect of the invention there is disclosed a training methodology for carrying out the methods described above.

Throughout the specification and claims which follow, unless the context requires otherwise, the word "comprise", and other variations such as "comprises" and "comprising", will be understood to imply the inclusion of a stated integer or step or group of integers or steps but not the exclusion of any other integer or step or group of integers of steps.

BRIEF DESCRIPTION OF THE DRAWINGS

A preferred embodiment of the invention will now be described, by way of example only, with reference to the accompanying drawings in which.

PREFERRED EMBODIMENT OF THE INVENTION

Figure 1:
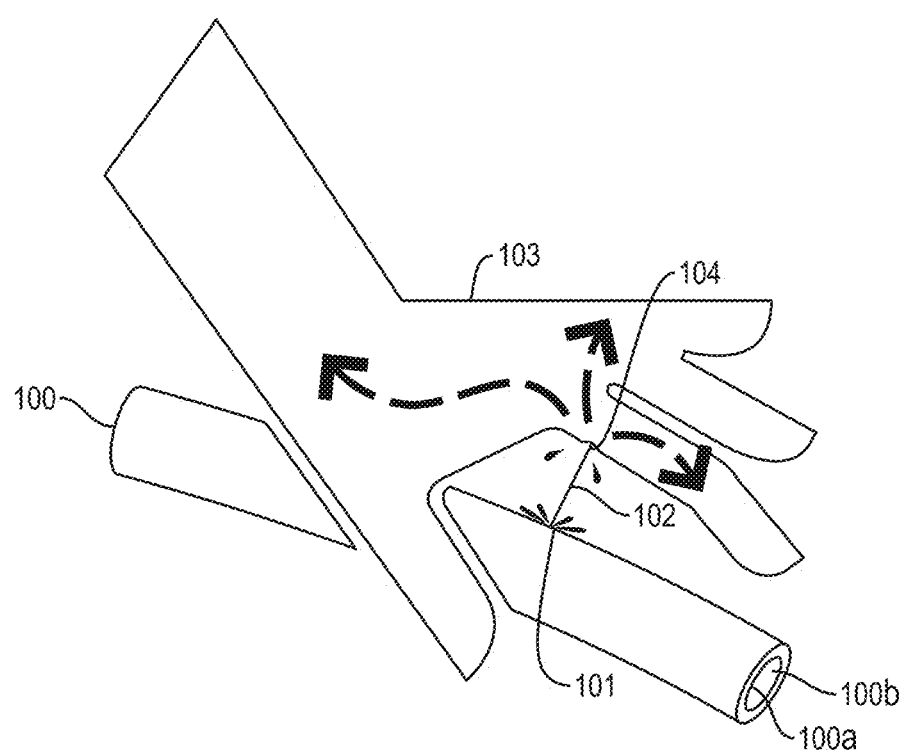
FIG. 1 is a view of a fluid injection according to the invention.

The preferred embodiment of the invention provides a method for detecting fluid injection in a patient following a possible fluid injection. The method including the step of providing a fluid storage tank in the form of equipment having a diesel or hydraulic tank. The appropriate fluid such as diesel or hydraulic fluid is added to the fluid storage tank. A fluorescent dye is then provided and adding to the fluid such that the fluid fluoresces in the presence of ultraviolet or blue light. It would be understood that the fluorescent dye can be added to any suitable fluid and the scope of the invention is not limited to diesel and hydraulic fluid.

The preferred embodiment of the invention also provides a fluid reservoir, the fluid reservoir adapted to store hydraulic fluid and fluorescent dye such that the hydraulic fluid and the fluorescent dye mix in the fluid reservoir. The fluid reservoir is connected to and is in fluid communication with at least one hydraulic actuator and/or motor such that the flow of hydraulic fluid and the fluorescent dye such drives the actuator and/or motor. As would be understood, the hydraulic system can be used to drive any number of motors, pumps and the like and many different types of machinery used in mining and in other applications. The fluid reservoir is connected to the at least one hydraulic actuator and/or motor by at least one of the following: a hydraulic tube; a hydraulic pipe; a hydraulic hose or the like such that a leak in the hydraulic tube, hydraulic pipe or hydraulic hose results in both hydraulic fluid and fluorescent dye leaking there from.

As would be understood, a broad spectrum of light could be used in embodiments of the invention and the invention is not limited to light of any particular wavelength or colour.

In the preferred embodiment the fluorescent dye used is sold under the brand name OIL-Oil Glo and is manufactured by T&T Global Solutions Pty Ltd. As would be understood any other suitable fluorescent dye can be used and chosen according to the particular application and specifications required.

Following a suspected fluid injection, the method includes the step of providing a fluorescent light to detect the presence of the fluid on a patient. In the preferred embodiment the light is a high intensity blue light although it would be understood that any suitable ultra violet light could be used. That is, following a suspected fluid injection of a person as a result of a high pressure stream of fluid from hydraulic machinery, if the person has been injected, hydraulic fluid mixed with the fluorescent dye would be injected into the patient. As a result of this injection with both hydraulic fluid and the dye, the injection point along with the injected tissue can be found using the ultra violet or blue light which causes the dye to fluoresce.

Once a suspected fluid injection occurs, the method includes the step of providing a dark room and examining the patient with the blue light in the dark room to determine whether possible fluid injection has occurred. After the initial examination, the method includes the step of washing the patient and particularly the point of possible fluid injection preferably with water and detergent.

After the step of washing the patient and the point of possible fluid injection, the method includes the step of re-examining the patient with the blue light in the dark room to determine whether possible fluid injection has occurred.

By following the steps of the preferred embodiment, it is possible to determine whether or not fluid injection has occurred in the patient.

FIG. 1 shows a view of a fluid injection according to the invention. Tubing 100 has pressurised fluid such as hydraulic fluid 100*a* flowing through it. The hydraulic fluid 100*a* has fluorescence 100*b* added to it. Tubing 100 includes a leak 101 that has resulted in a high pressure leak 102. In this instance a patient's hand 103 is in the way of the stream and the hand 103 receives a fluid injection through injection point 104.

Following the fluid injection the following steps are followed:

1. Confirm the fluid has the recommended OIL-GLO® fluorescent dye product and is as per the design application schedule. Specifically does the fluid that's escaped under pressure visibly glow when exposed to blue or ultraviolet light.
2. If suspected fluid injection occurs immediately follow any fluid injection protocol and utilise the high intensity blue light on the surface of the area.
3. Confirm that Paramedics on site or in attendance are conversant with the use of the blue light.
4. Ensure that the person that has potentially received a fluid injection is taken to a dark environment and scanned with the approved blue light prior to washing the affected area.
5. Wash the affected area utilising copious amounts of water and any industrial hand and face soap or detergent.
6. Ensure that the person that has potentially received a fluid injection is taken to a dark environment after washing and scanned with the approved blue light.
7. If no detection of OIL-GLO® fluorescent dye is present on the surface of the skin follow the sites fluid injection protocol.
8. If fluorescence is detected on the surface of the skin then the patient should be taken for immediate medical care to have the fluid removed through surgery or other suitable manners.

The following examples show test results of fluid escaping under pressure at a distance of 0 mm↔1.00 mm, an escape pressure of 10 bar increasing to 207 Bar and a flow rate of 2.2 1 pm. The fluid used is Fuchs Solcenic 20/20 with a ratio of 98% water 2% Solcenic.

Figure 2:
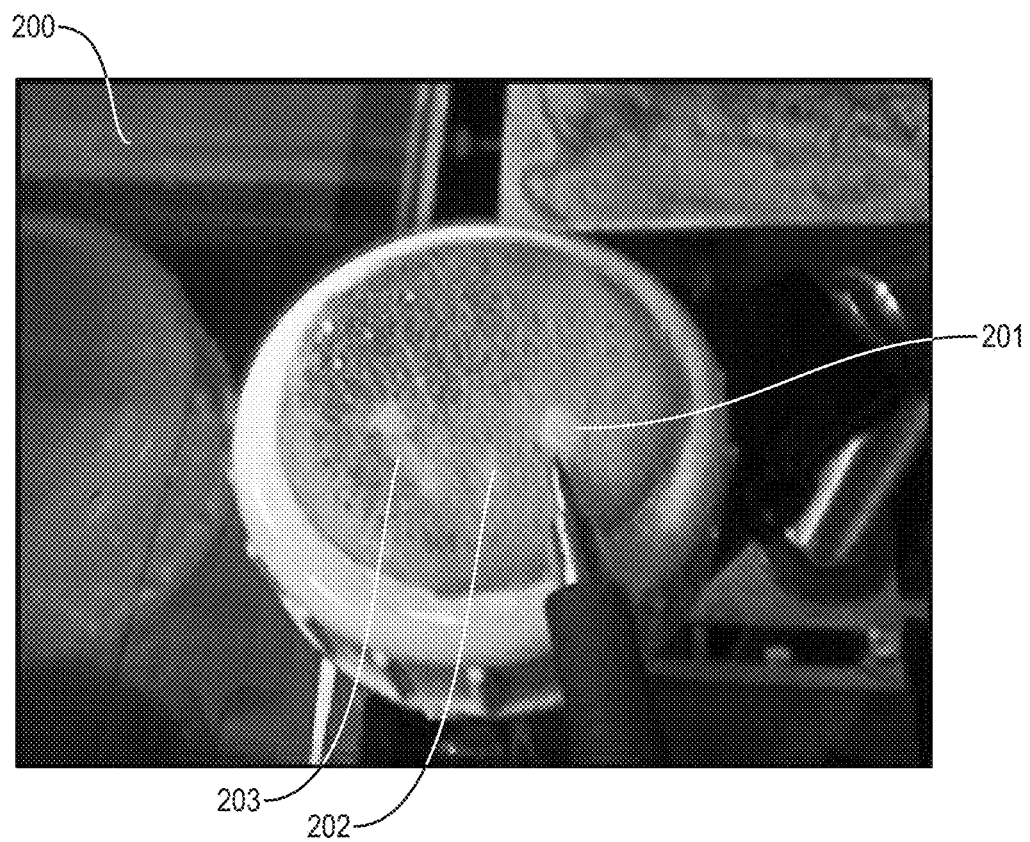
FIG. 2 a picture of a fluid injection according to the invention.

Referring to FIG. 2 there is shown a tissue sample 200 under blue light that has received a fluid injection. In this example, evidence visible after affected area has been washed indicates a fluid injection has occurred. In this example the penetration of human skin occurs at 172 Bar (2500 psi) @ 100 mm @ 2.2 1 pm.

Figure 3:
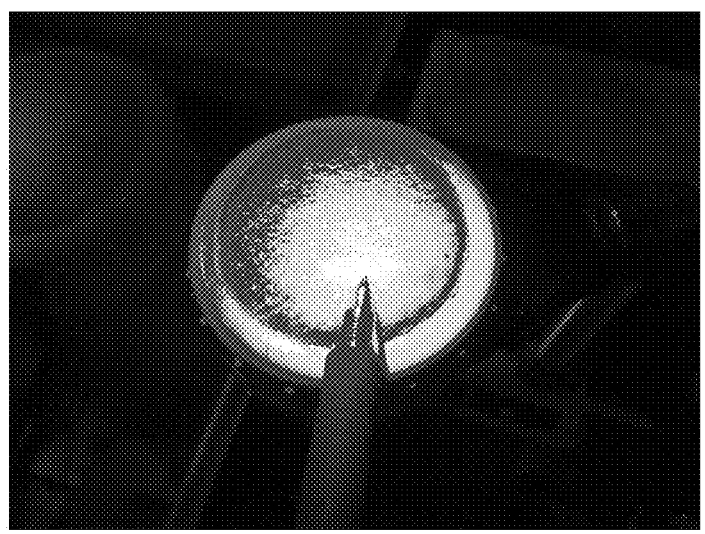
FIG. 3 shows a tissue sample according to the invention.

FIG. 3 shows penetration of human skin at 138 Bar (2000 psi) 100 mm 2.2 1 pm.

Figure 4:
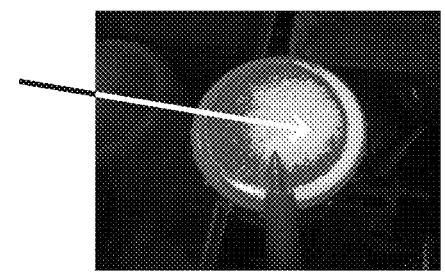
FIG. 4 shows a tissue sample according to the invention.

FIG. 4 shows penetration of human skin at 103 Bar (1500 psi) @ 100 mm @ 2.2 1 pm. This photo represents the surface of the tissue and clearly highlights an injection from the underside of the tissue.

Figure 5:
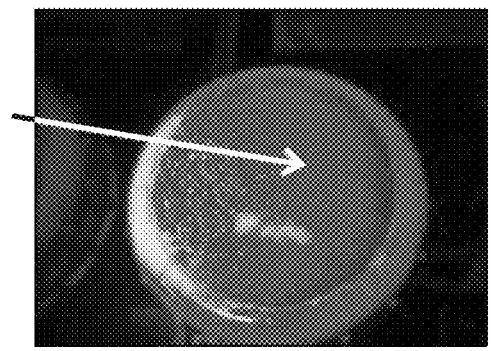
FIG. 5 shows a tissue sample according to the invention.

FIG. 5 shows penetration of human skin at 34 Bar (500 psi) @ 100 mm @ 2.2 1 pm. This photo represents the surface tissue and clearly highlights an injection under the surface of the tissue.

Figure 6A:
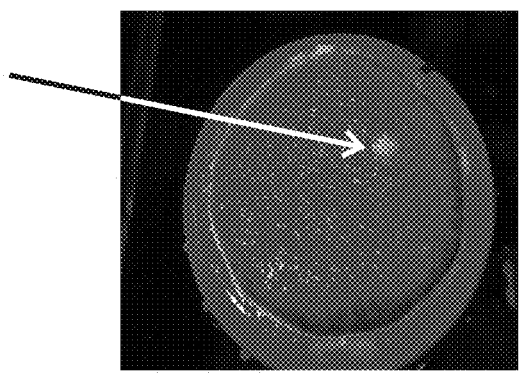
FIGS. 6a and 6b show a tissue sample according to the invention.
Figure 6B:
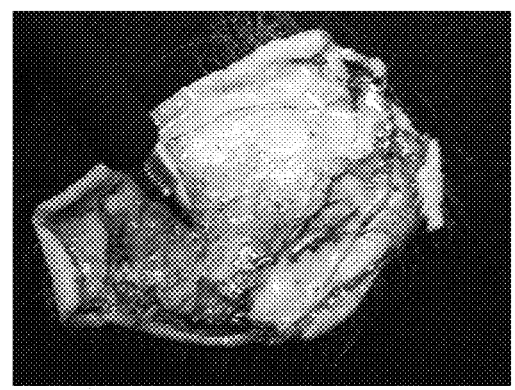

FIGS. 6*a* and 6*b* show penetration of human skin at 10 Bar (145 psi) @ 100 mm @ 2.2 1 pm. FIG. 6*a* shows the surface of the tissue and is clearly visible under UV light and associated Glo products. FIG. 6*b* represents the underside of the tissue and is visible under UV light and associated OIL-GLO® fluorescent dye products.

Figure 7A:
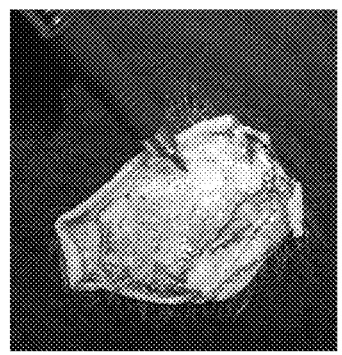
FIGS. 7a and 7b show a tissue sample according to the invention.
Figure 7B:
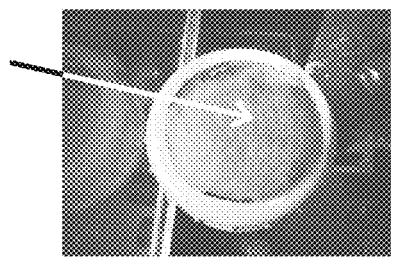

FIGS. 7*a* and 7*b* show penetration of human skin at 10 Bar (145 psi) @ 50 mm @ 2.2 1 pm. FIG. 7*a* represents the underside of the tissue and clearly highlights that fluid will break the skin. FIG. 7*b* represents the surface of the tissue and is visible under UV light and associated OIL-GLO® fluorescent dye products.

In relation to the samples shown above, the oil was injected under pressure from the underside of each sample.

Figure 8A:
FIGS. 8a and 8b show a fluid according to the invention.
Figure 8B:
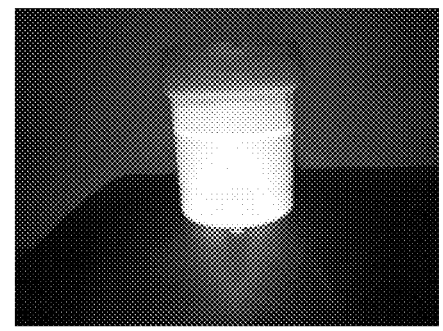

FIG. 8*a* shows a sample of standard hydraulic oil (ISO 68) photographed under high intensity blue light. FIG. 8*b* shows the sample of standard hydraulic oil (ISO 68) with 0.20% OIL-GLO® fluorescent dye additive photographed under high intensity blue light.

Figure 9A:
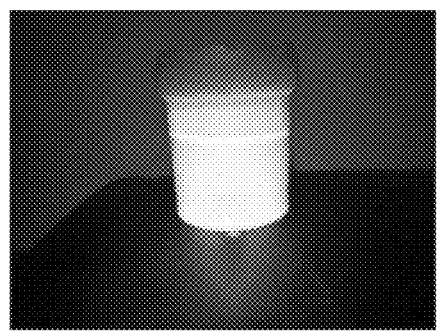
FIGS. 9a and 9b show a fluid according to the invention.
Figure 9B:
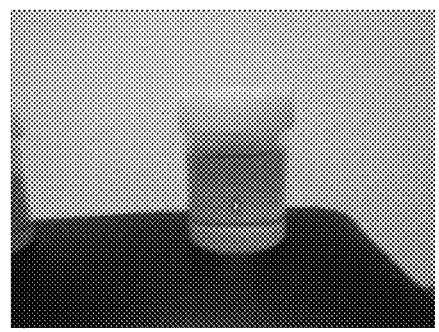

FIG. 9*a* shows a sample of 100% Solcenic photographed under high intensity blue light. FIG. 9*b* shows the sample of 100% Solcenic with the OIL-GLO® fluorescent dye additive @ 0.01% and photographed under high intensity blue light.

The preferred embodiment of the invention advantageously allows reliable detected in deep tissues which allows triage of cases not requiring surgery and also guides any surgery required thus potentially limiting the soft tissue surgical dissection required.

Embodiments of the invention extend to kits supplied with lights to detect the presence of the fluorescent dye in a patient.

Figure 10:
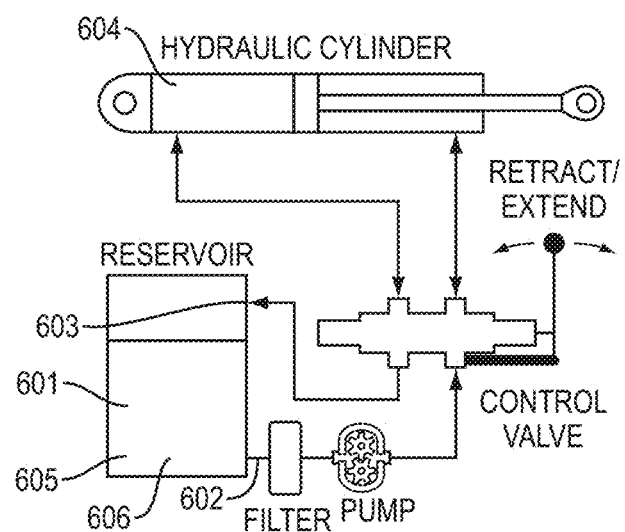
FIG. 10 shows a hydraulic system according to the invention.

FIG. 10 shows a typical hydraulic system with a reservoir tank 601, outlet 602 and inlet 603. Hydraulic fluid 606 is pumped out the outlet 602 and through the hydraulic circuit which drives hydraulic cylinder 604. According to preferred embodiments, fluorescent dye 605 is added to the hydraulic fluid 606 preferably by adding it into the reservoir tank 601. The hydraulic fluid 606 and the dye 605 then mix and both the fluid and the dye are pumped around the hydraulic circuit. Accordingly if there is a leak at any point in the system the mixture of both hydraulic fluid and dye is expelled through any leaks. According to the application this allows leaks to be detected and allows fluid injection in any patients to be detected in accordance with the disclosure above.

Further embodiments of the invention extend to systems and method for detecting leaks in hydraulic systems. In a similar manner as described above, a suitable dye (not necessarily, fluorescent) can be added to the hydraulic tank of machinery such that the dye colours the hydraulic liquid causing it to take on the colour characteristics of the dye. The dye need not in these embodiments be fluorescent but could be chosen according to colour characteristics that could be easily seen in the specific environment in which the machinery operates. In addition, embodiments of the invention include any number of liquids to which the dye could be added. For example diesel, petrol, oil, water are just some of the liquids to which a suitable dye could be added according to embodiments of the invention.

Advantages of the invention include the following:
Long term injury's are significantly reduced as this may be used as the first protocol on site for identification of any suspected fluid injection injury prior to any additional medical treatment;
Environmentally safe;
Soluble with all mineral oils, emulsions, gear oils, water and engine oil (MSDS included);
Increases machine availability (highlights oil leaks);
Endorsed by major OEM'S and currently used for life of machine in all hydraulic systems;

Highly visible on the surface of the human skin;
Highly visible in soft tissue underneath the human skin;
Approved UV or blue light can also be used for NDT in many other engineering applications; and
Reduces surgery and rehabilitation as this product is highly visible on and under the skin as described above.

Although the invention has been described with reference to specific examples, it will be appreciated by those skilled in the art that the invention may be embodied in many other forms.

What is claimed is:

1. A method for detecting an accidental industrial fluid injection in a patient by machinery that operates under high pressure, the method including the steps of:
    providing the industrial fluid for use in the machinery;
    adding a fluorescent dye to the industrial fluid such that the fluid fluoresces in the presence of a high-intensity blue light;
    adding the industrial fluid to a fluid storage tank;
    providing a lamp emitting high-intensity blue light, wherein the high-intensity blue light causes the industrial fluid with the fluorescent solution dye to fluoresce;
    examining the patient with the high-intensity blue light in a dark environment following a possible accidental fluid injection; and
    detecting a presence of fluorescence in the patient wherein the high-intensity blue light causes the fluorescent dye to fluoresce, wherein the presence of the fluorescence in the patient indicates a possible accidental industrial fluid injection.

2. A method according to claim 1 including the step of a possible fluid injection occurring in a patient.

3. The method according to claim 1 including the step of examining the patient with the high-intensity blue light in the dark environment further comprises the step of washing a potentially fluid-injected affected area of the patient.

4. The method according to claim 3, wherein the patient is examined with the high-intensity blue light before washing the potentially fluid-injected affected area on the patient, after washing the potentially fluid-injected affected area on the patient, or both before and after washing the potentially fluid-injected affected area on the patient.

5. The method according to claim 3, wherein the step of examining the patient with the high-intensity blue light in the dark environment further comprises inspecting, with the high-intensity blue light, an area of skin around the potentially fluid-injected affected area on the patient.

6. The method according to claim 1, further comprising determining that the accidental industrial fluid injection has occurred in the patient by detecting fluorescence of the fluorescent dye of the industrial fluid under skin of the patient.

7. The method of claim 6, wherein the accidental industrial fluid injection occurred in the patient upon a pressurized release of the industrial fluid from the machinery.

8. The method of claim 6, wherein the industrial fluid for use in machinery is hydraulic fluid or fuel.

9. The method of claim 6, wherein the machinery is hydraulic machinery having a fluid storage tank, wherein the fluid storage tank is connected to, and in fluid communication with a hydraulic actuator, a hydraulic motor, or both, and wherein the fluid communication is through a hydraulic tube, a hydraulic pipe, or a hydraulic hose.

10. The method of claim 9, wherein the industrial fluid is hydraulic fluid, and wherein flow of hydraulic fluid drives the hydraulic actuator, the hydraulic motor, or both.

* * * * *